US00PP09166P

United States Patent [19]

van der Knaap

[11] Patent Number: Plant 9,166

[45] Date of Patent: Jun. 13, 1995

[54] CHRYSANTHEMUM PLANT NAMED 'CHAMPION'

[75] Inventor: Jacques C. M. van der Knaap, De Lier, Netherlands

[73] Assignee: Fides Beheer B.V., De Lier, Netherlands

[21] Appl. No.: 202,201

[22] Filed: Feb. 25, 1994

[51] Int. Cl.[6] ..... A01H 5/00

[52] U.S. Cl. ..... Plt./74.1

[58] Field of Search ..... Plt. 74.1, 82.4, 82.5

[56] References Cited

U.S. PATENT DOCUMENTS

P.P. 6,944 7/1989 van den Berg ..... Plt./82.5
P.P. 8,042 11/1992 van der Knaap ..... Plt./74.1
P.P. 8,641 3/1994 van der Knaap ..... Plt./74.1

*Primary Examiner*—Howard J. Locker
*Attorney, Agent, or Firm*—Burns, Doane, Swecker & Mathis

[57] ABSTRACT

A new and distinct cultivar of Chrysanthemum plant named Champion is provided. The new cultivar was the result of a controlled breeding program. The new cultivar forms attractive flat bi-toned pink anemone flowers with a more intense coloration at the cushion. The plant exhibits a reduced susceptibility to leafminers, and the flowers exhibit a good vase life. The response period of the flowers is approximately seven to eight weeks. The new cultivar is particularly suited for use in the production throughout the year of a cut anemone spray or a pot mum under greenhouse conditions. An excellent tolerance to high temperature is exhibited.

1 Drawing Sheet

SUMMARY OF THE INVENTION

The present invention comprises a new and distinct cultivar of Chrysanthemum, botanically known as *Chrysanthemum morifolium,* Ramat., and hereinafter is referred to by the cultivar name Champion. Alternatively, the botanical classification sometimes is expressed as *Dendranthema indicum.*

The new cultivar is the product of a planned breeding program which had as its objective the creation of a new Chrysanthemum cultivar which exhibits attractive anemone flowers having a distinctive bi-tones coloration, a flower response period of approximately eight weeks, a good breaking ability, and the ability to produce flowers of commercially acceptable quality throughout the year in a cut mum or a pot mum production program especially when grown in a 12 cm. pot. Such combination of traits is not believed to have been present in the previously available Chrysanthemum cultivars. This objective was satisfactorily fulfilled in the cultivar of the present invention.

The breeding program which resulted in the production of the new cultivar of the present invention was carried out in a controlled environment during 1988 at De Lier, The Netherlands. The female parent (i.e., the seed parent) was an unnamed plant designated 88.2345 (non-patented in the United Sates), and the male parent (i.e., the pollen parent) was the Toon Hermans cultivar (non-patented in the United States). The parentage of the new cultivar can be summarized as follows:

88.2345 × Toon Hermans.

The seeds resulting from the above pollination were sown and plantlets were obtained which were physically and biologically different from each other. Selective study during May 1988 resulted in the identification of a single plant of the new variety.

It was found that the new Chrysanthemum cultivar of the present invention:

(a) exhibits attractive flat bi-toned pink anemone flowers wherein the disc florets are darker than the ray florets,
(b) exhibits a flower response period of approximately seven to eight weeks,
(c) forms flowers that exhibit a good vase life,
(d) exhibits a reduced susceptibility to leafminers, and
(e) has the ability to produce flowers of commercially acceptable quality throughout the year.

The susceptability to leafminers of the new cultivar is less than that of the standard resistant Penny Lane cultivar (U.S. Plant Pat. No. 6,238) and is more resistant than that of the standard susceptible Dark Pink Pompon cultivar (non-patented in the United States).

The new cultivar exhibits an excellent tolerance to high temperatures. Commonly Chrysanthemum plants are grown in greenhouses in The Netherlands while using nightime temperatures of approximately 18° to 20° C., and daytime temperatures of approximately 18° C. with ventilation from 22° C. The Champion cultivar has been successfully grown during the summer in greenhouses wherein the temperature is approximately 6° C. higher during the daytime.

The susceptibility to leafminers of the new cultivar is less than that of the standard resistant Penny Lane cultivar (U.S. Plant Pat. No. 6,238) and is more resistant than that of the standard susceptible Dark Pink Pompon cultivar (non-patented in the United States).

Asexual reproduction of the new cultivar by vegetative cuttings initially taken during June 1988, as performed at De Lier, The Netherlands, in a controlled environment has demonstrated that the characteristics of the new cultivar as here disclosed are firmly fixed and are retained through successive generations of asexual propagation.

Champion has not been observed under all possible environmental conditions to date. Accordingly, it is possible that the phenotype may vary somewhat with variations in the environment, such as temperature, light intensity, day length, contact with pesticides, and/or subjection to growth retardant treatments.

When the new cultivar of the present invention is compared to the Tasca cultivar (U.S. Plant Pat. No. 6,944) the Champion cultivar is found to exhibit a smaller flower size, a shorter response period, and a more intense coloration of the ray florets. The anemone type of flower, abundance of flowering, and excellent tolerance to high temperatures are similar to that exhibited by the Tasca cultivar.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown under greenhouse conditions at De Lier, The Netherlands.

DETAILED DESCRIPTION

The chart used in the identification of colors described hereafter is the R.H.S. Colour Chart of The Royal Horticultural Society, London, England. The color values were determined at 11:00 a.m. under natural daylight conditions at De Lier, The Netherlands, during April of 1992. The plants described were grown under standard greenhouse conditions which approximate those commonly utilized for the production of cut mums.

Classification:

*Botanical.*—*Chrysanthemum morifolium* Ramat., cv. Champion.

*Commercial.*—Cut anemona spray, or pot mum.

Inflorescence:

A. Capitulm.—Form. — Flat. Type. — Anemone. Diameter across face.—Approximately 35 mm. on average. *Diameter across disc.*—Varies considerably and commonly can range from approximately 8 to 35 mm. under greenhouse growing conditions.

B. *Corolla of ray and disc florets.*—Color (General tonality from a distance of three meters). — Pink with the adaxial coloration commonly being a lighter pink. *Color disc florets.*—Approaches Red-Purple Group 63A. *Color ray florets.*—Approaches Red-Purple Group 68A on the upper surface and Red-Purple Group 69A on the under surface.

C. *Reproductive organs.*—*Androecium.* — Not present. *Gynoecium.* — Present in disc florets and in ray florets.

Plant:

A. *General Appearance.*—Height. — Medium tall. A height of approximately 30 to 40 cm. commonly is achieved throughout the year while utilizing an Alar growth retardant.

B. Foliage.—Color (abaxial). — Green Group 138A. Color (adaxial) — Green Group 137A to b 137B. *Shape.*—Cordate.

I claim:

1. A new and distinct cultivar of Chrysanthemum plant named Champion substantially as herein shown and described, which:

(a) exhibits attractive flat bi-toned pink anemone flowers wherein the disc florets are darker than the ray florets,
(b) exhibits a flower response period of approximately seven to eight weeks,
(c) forms flowers that exhibit a good vase life,
(d) exhibits a reduced susceptibility to leafminers, and
(e) has the ability to produce flowers of commercially acceptable quality throughout the year.

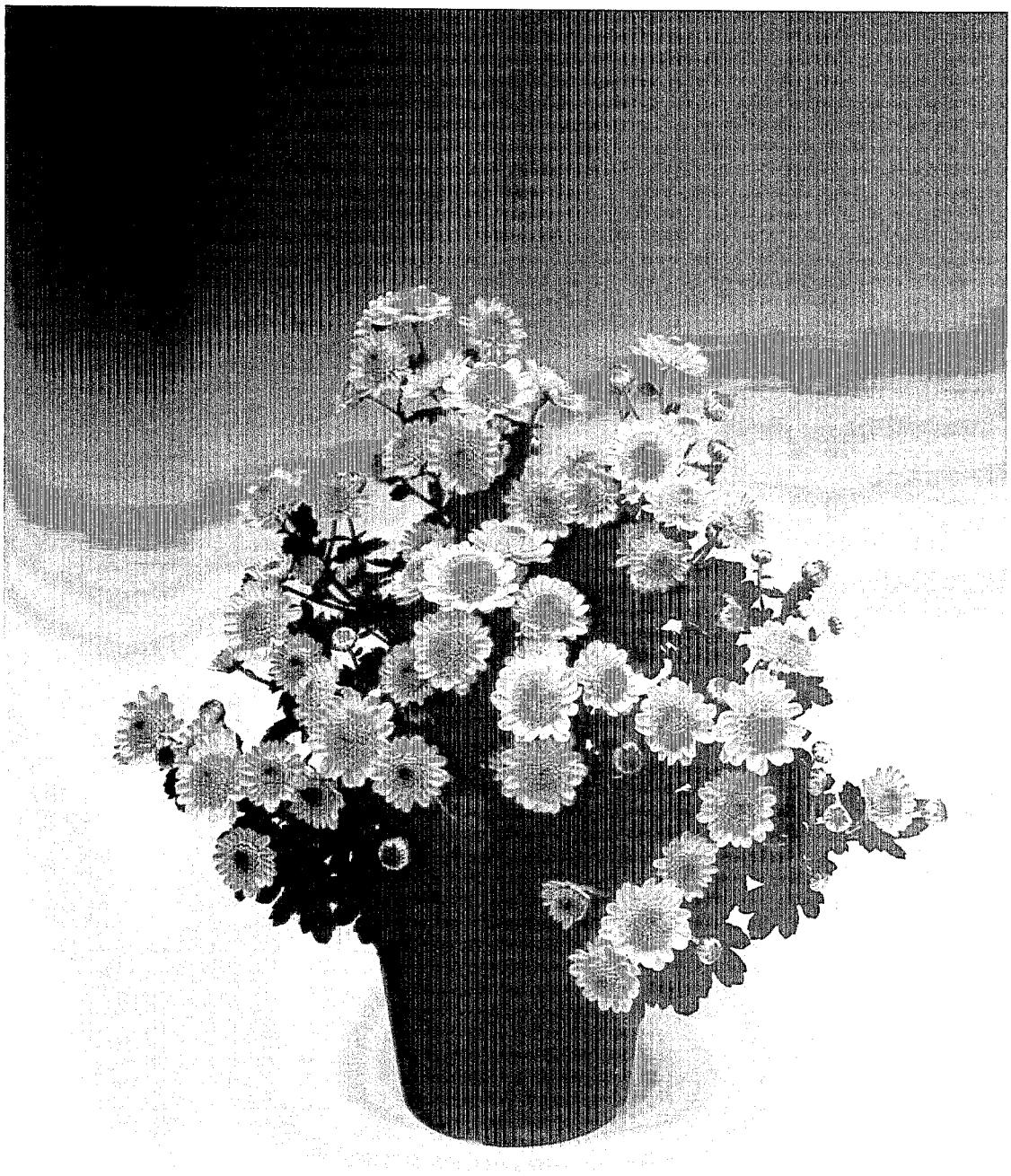

* * * * *